(12) United States Patent
Gallop et al.

(10) Patent No.: US 10,909,771 B2
(45) Date of Patent: Feb. 2, 2021

(54) SYSTEM AND METHOD FOR IMAGE PROCESSING

(71) Applicants: David Gallop, Toronto (CA); Wesley Bryan Hodges, Toronto (CA)

(72) Inventors: David Gallop, Toronto (CA); Wesley Bryan Hodges, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 151 days.

(21) Appl. No.: 15/510,175

(22) PCT Filed: Sep. 15, 2014

(86) PCT No.: PCT/CA2014/000690
§ 371 (c)(1),
(2) Date: Mar. 9, 2017

(87) PCT Pub. No.: WO2016/041045
PCT Pub. Date: Mar. 24, 2016

(65) Prior Publication Data
US 2017/0249786 A1    Aug. 31, 2017

(51) Int. Cl.
*G01R 33/48* (2006.01)
*A61B 8/08* (2006.01)
(Continued)

(52) U.S. Cl.
CPC ............ *G06T 19/20* (2013.01); *A61B 5/0042* (2013.01); *A61B 5/055* (2013.01); *A61B 5/742* (2013.01);
(Continued)

(58) Field of Classification Search
CPC ....... A61B 8/483; A61B 34/20; A61B 34/105; A61B 5/055; A61B 8/463; A61B 8/466;
(Continued)

(56) References Cited

U.S. PATENT DOCUMENTS 8,083,680 B2    12/2011  Choi
2008/0177182 A1*  7/2008  Takimoto ................. A61B 8/06
                                                    600/441
(Continued)

OTHER PUBLICATIONS

International Search Report dated May 15, 2015 issued from the Canadian Intellectual Property Office relating to PCT International Application No. PCT/CA2014/000690.
(Continued)

*Primary Examiner* — Allen Porter
*Assistant Examiner* — Adreanne A. Arnold
(74) *Attorney, Agent, or Firm* — Perry + Currier

(57) ABSTRACT

Mechanisms for image processing are provided. A computing device comprises a memory, an input device, a display, and a processor. The processor is configured to: acquire a three-dimensional image of an anatomical structure and store it in the memory. The processor renders on the display (i) an initial volume of the three-dimensional image corresponding to an initial portion of the anatomical structure, and (ii) a moveable control element. The initial volume has an outer surface defined by a position of the control element. The processor receives input data updating the position of the control element relative to the initial volume; and renders on the display, in place of the initial volume, a further volume of the three-dimensional image, corresponding to a further portion of the anatomical structure and having a further outer surface defined by the updated position of the control element.

6 Claims, 10 Drawing Sheets

(51) Int. Cl.
- *A61B 5/00* (2006.01)
- *G06T 19/20* (2011.01)
- *G01R 33/56* (2006.01)
- *A61B 5/055* (2006.01)
- *G06T 19/00* (2011.01)
- *A61B 6/03* (2006.01)

(52) U.S. Cl.
CPC .......... *G01R 33/5608* (2013.01); *G06T 19/00* (2013.01); *A61B 5/0066* (2013.01); *A61B 6/032* (2013.01); *A61B 8/0808* (2013.01); *A61B 2576/026* (2013.01)

(58) Field of Classification Search
CPC ....... A61B 8/5223; A61B 34/25; A61B 34/30; A61B 5/742; A61B 6/032; A61B 8/085
See application file for complete search history.

(56) References Cited

U.S. PATENT DOCUMENTS

| 2011/0107270 A1* | 5/2011 | Wang ................ G06F 19/3481 715/850 |
| 2012/0078102 A1 | 3/2012 | Lee |
| 2013/0021336 A1* | 1/2013 | Tsukagoshi ............ A61B 6/462 345/419 |
| 2014/0063208 A1 | 3/2014 | Fukasawa et al. |
| 2014/0071132 A1 | 3/2014 | Noshi et al. |

OTHER PUBLICATIONS

Written Opinion dated May 15, 2015 issued from the Canadian Intellectual Property Office relating to PCT International Application No. PCT/CA2014/000690.

International Preliminary Report on Patentability dated Sep. 3, 2015 issued from the Canadian Intellectual Property Office relating to PCT International Application No. PCT/CA2014/000690.

* cited by examiner

SYSTEM AND METHOD FOR IMAGE PROCESSING

FIELD

The specification relates generally to medical imaging, and specifically to a computing device, system and method for image processing.

BACKGROUND

The planning and execution of surgical procedures, particularly complex procedures such as brain surgery, may require the gathering and organization of large volumes of information, including various medical images of the patient. Such images can include, for example, MRI scans.

Accessing such information, particularly during a surgical procedure, may require extensive preparation of different image views prior to the procedure; in other cases, significant portions of the images may simply not be available during the procedure, or may require additional operators and time-consuming programming and computational efforts to produce.

SUMMARY

According to an aspect of the specification, a computing device is provided, comprising: a memory; an input device; a display; and a processor interconnected with the memory, the input device and the display, the processor configured to: acquire a three-dimensional image of an anatomical structure of a patient and store the three-dimensional image in the memory; render on the display (i) an initial volume of the three-dimensional image corresponding to an initial portion of the anatomical structure, and (ii) a moveable control element; the initial volume having an initial outer surface defined by a position of the control element; receive, from the input device, input data updating the position of the control element on the display relative to the initial volume; responsive to receiving the input data, render on the display, in place of the initial volume, a further volume of the three-dimensional image, corresponding to a further portion of the anatomical structure and having a further outer surface defined by the updated position of the control element; the processor configured to select the further volume by identifying a portion of the three-dimensional images that intersects with the at least one plane or volume, and excluding the identified portion from the further volume.

According to another aspect of the specification, method is provided of processing images in a computing device having a memory, an input device, a display and a processor interconnected with the memory, the input device and the display, the method comprising: acquiring a three-dimensional image of an anatomical structure of a patient and storing the three-dimensional image in the memory; at the processor, rendering on the display (i) an initial volume of the three-dimensional image corresponding to an initial portion of the anatomical structure, and (ii) a moveable control element; the initial volume having an initial outer surface defined by a position of the control element; receiving, at the processor from the input device, input data updating the position of the control element on the display relative to the initial volume; responsive to receiving the input data, controlling the display at the processor to render, in place of the initial volume, a further volume of the three-dimensional image, corresponding to a further portion of the anatomical structure and having a further outer surface defined by the updated position of the control element.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art.

Figure 1:
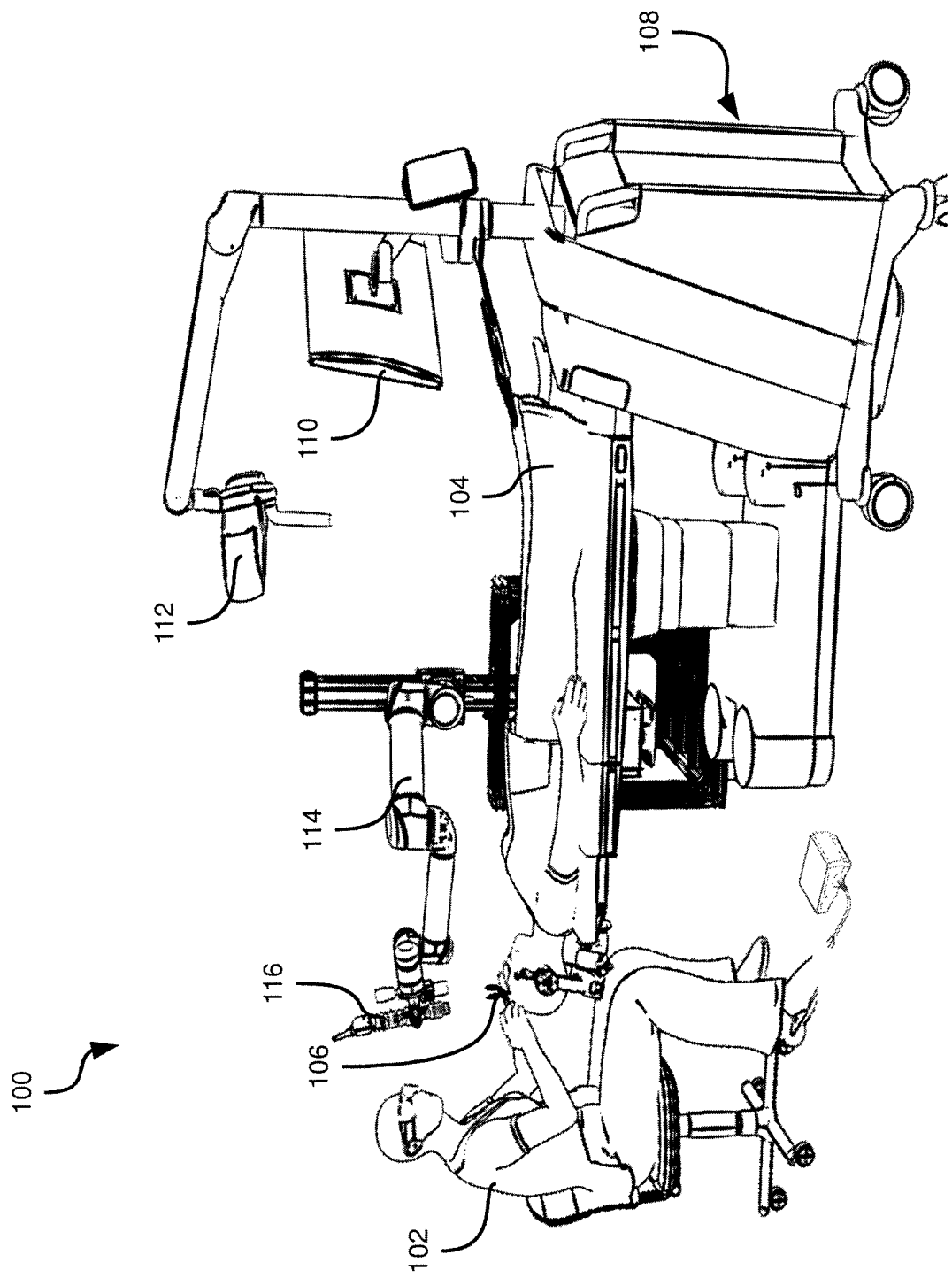
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device. The computing device, display 110, or both, may also be supported by other structures. Indeed, the computing device may be located outside of operating theatre 100, and where multiple displays are provided, at least one display may also be located outside of operating theatre 100.

Equipment tower 108 may also support a tracking system 112. Tracking system 112, when included, is generally configured to track the positions of one or more reflective markers (not shown) mounted on access port 106, any of the above-mentioned surgical tools, or any combination thereof. Such markers, also referred to as fiducial markers, may also be mounted on patient 104, for example at various points on patient 104's head. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 106 by robotic arm 114, and may capture images of the brain of patient 104 for presentation on display 110. The movement of robotic arm 114 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Both before and during a surgical procedure such as the one illustrated in FIG. 1, images of anatomical structures within patient 104 may be obtained using various imaging modalities. For example, images of the brain of patient 104 may be obtained using Magnetic Resonance Imaging (MRI), Optical Coherence Tomography (OCT), ultrasound, Computed Tomography (CT), optical spectroscopy and the like. As will be discussed in further detail below, such images may be stored in the computing device mentioned above, and subsequently processed by the computing device for presentation and manipulation on display 110.

Figure 2:
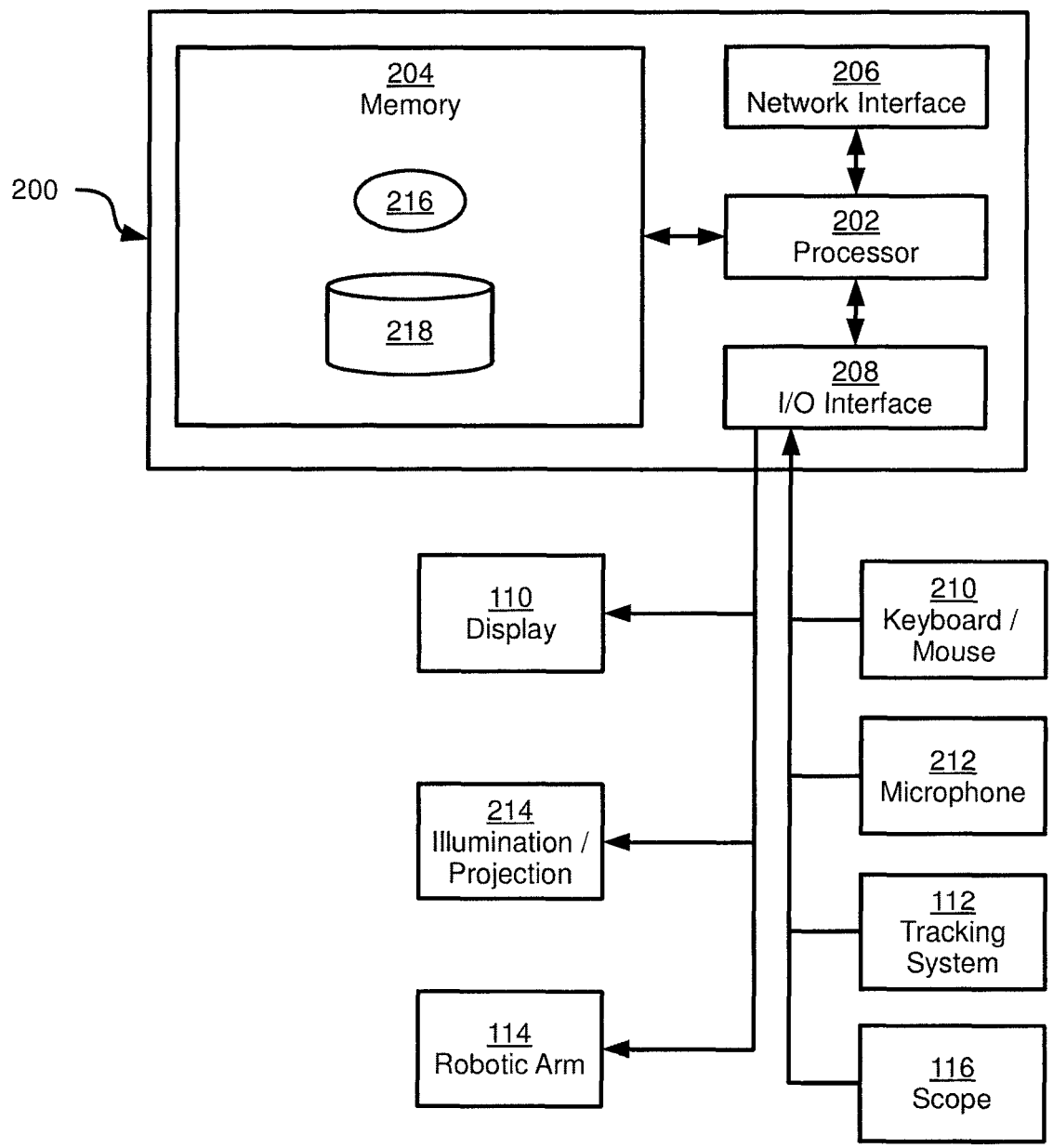
FIG. 2 depicts a computing device for deployment in the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 can also include a network interface 206 interconnected with processor 200. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 can also include an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components. In general, I/O interface 208 connects computing device 200 to "local" input and output devices, while network interface 206 connects computing device 200 to "remote" computing devices, which may themselves be connected to additional input and output devices. This arrangement may be varied, however. For example, any suitable combination of the input and output devices to be discussed below may be connected to computing device 200 via network interface 206 rather than I/O interface 208. Indeed, in some embodiments I/O interface 208 may be omitted entirely, while in other embodiments network interface 206 may be omitted entirely.

In the present example, via interface 208, computing device 200 can be connected to input devices including a keyboard and mouse 210, a microphone 212, as well as scope 116 and tracking system 112, mentioned above. Also via interface 208, computing device 200 can be connected to output devices including illumination or projection components 214 (e.g. lights, projectors and the like), as well as display 110 and robotic arm 114 mentioned above. It is contemplated that other combinations of devices may also be present, omitting one or more of the above devices, including other input (e.g. touch screens) and output (e.g. speakers, printers) devices, and the like.

Computing device 200 stores, in memory 204, an image manipulation application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 is a patient data repository 218. Patient data repository 218 can contain a surgical plan defining the various steps of the minimally invasive surgical procedure to be conducted on patient 104, as well as images of patient 104 (e.g. MRI and CT scans).

As mentioned above, computing device 200 is configured, via the execution of application 216 by processor 202, to perform various functions related to presenting and manipulating images of patient 104 on display 110. Those functions will be described in further detail below.

Figure 3:
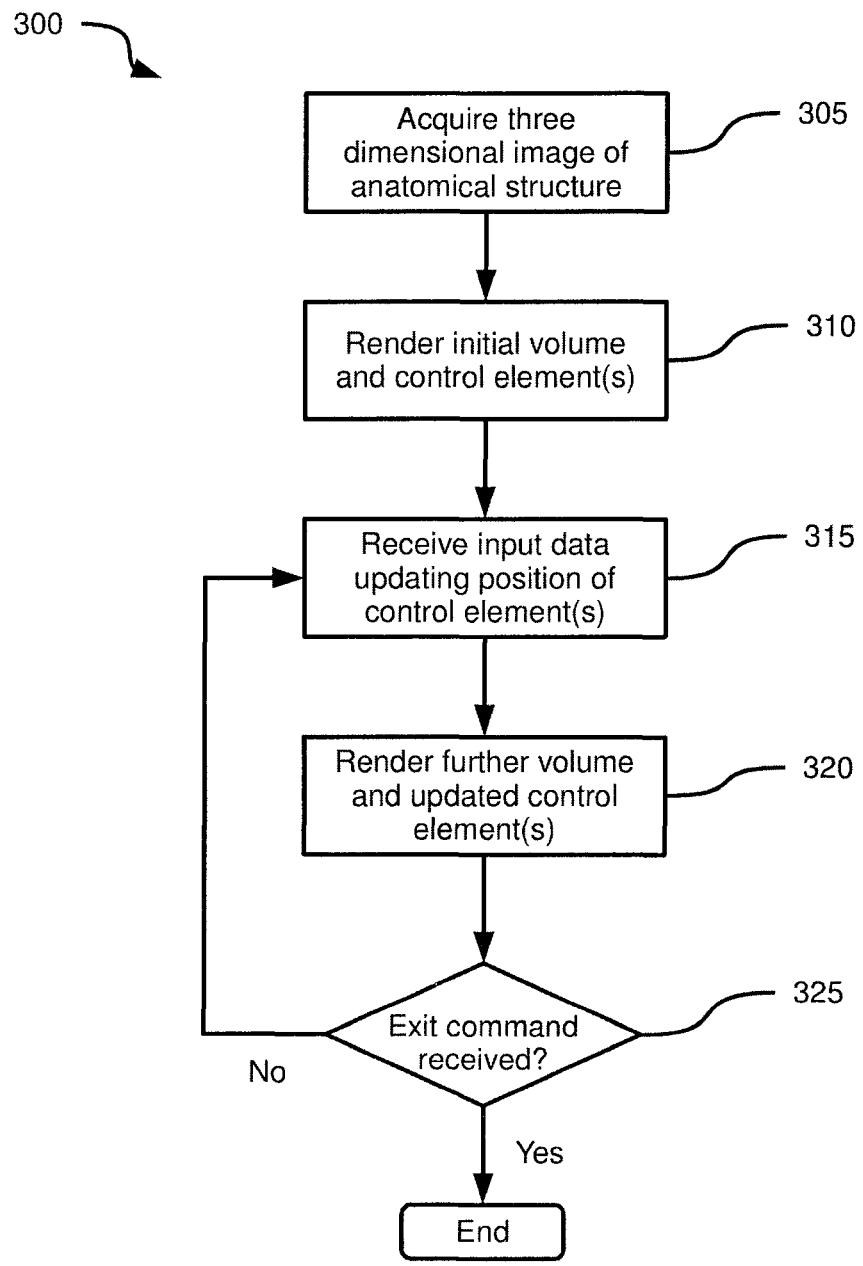
FIG. 3 depicts a method of processing images, according to a non-limiting embodiment.

Referring now to FIG. 3, a method 300 of processing images is depicted. Method 300 will be discussed in conjunction with its performance on computing device 200 as deployed in operating theatre 100. It will be apparent to those skilled in the art, however, that method 300 can also be implemented on other computing devices in other systems.

Beginning at block 305, computing device 200 is configured to acquire at least one three-dimensional image of an anatomical structure of patient 104 and store the three-dimensional image in memory 204 (for example, in patient data repository 218). In the present example, the anatomical structure is the brain of patient 104, but a variety of other anatomical structures may also be imaged instead of, or in addition to, the brain. The mechanism of acquisition of the image is not particularly limited. For example, computing device 200 can obtain the image directly from an imaging device (not shown), such as an MRI scanner. In other examples, computing device 200 can obtain the image from another computing device which itself obtained the image from an imaging device.

The exact nature of the image may also vary. In the present example, the three-dimensional image is assumed to be an MRI scan. The collection of two-dimensional MRI slices, together representing a three-dimensional scan of the brain, is referred to herein as the three-dimensional image. In other examples other imaging modalities may be employed instead of, or in addition to, MRI.

Proceeding to block 310, computing device 200 is configured to control display 110 (e.g. via I/O interface 208) to render an interface for presenting and manipulating the three-dimensional image. In general, the interface includes a rendering of an initial volume of the three-dimensional image corresponding to an initial portion of the anatomical structure (that is, the brain of patient 104). The interface rendered at block 310 also includes at least one moveable control element, which will be discussed in greater detail below. Broadly, the initial volume rendered on display 110 has an initial outer surface defined by a position of the control element relative to the initial volume.

In other words, the three-dimensional image contains data depicting a given volume of the anatomical structure. In the case of the brain, the three-dimensional image may in fact depict a volume of patient 104 that is larger than the brain itself. An MRI scan of the brain, for example, can depict the skull as well as the brain. The initial volume rendered on display 110 at block 310 need not contain the entire volume of the three-dimensional image (although it may contain the entire volume). The initial volume referred to above, therefore, is some portion (up to and including 100%) of the three-dimensional image. Which portion of the three-dimensional image is rendered at block 310 is computed by processor 204 based on the positions of the above-mentioned control elements.

As will be discussed in greater detail below, the control elements define geometrical planes or volumes having positions relative to the three-dimensional image (e.g. coordinates within a coordinate system associated with the three-dimensional image). At those positions, the planes or volumes defined by the control elements intersect with the volume of the three-dimensional image. Such intersections define the outer surface of the initial volume to be rendered from the complete three-dimensional image. That is, the intersections of the control elements with the three-dimensional image define the boundaries of the initial volume to be rendered (i.e. what portion of the image will be rendered and what portion will be excluded from the rendering).

Figure 4:
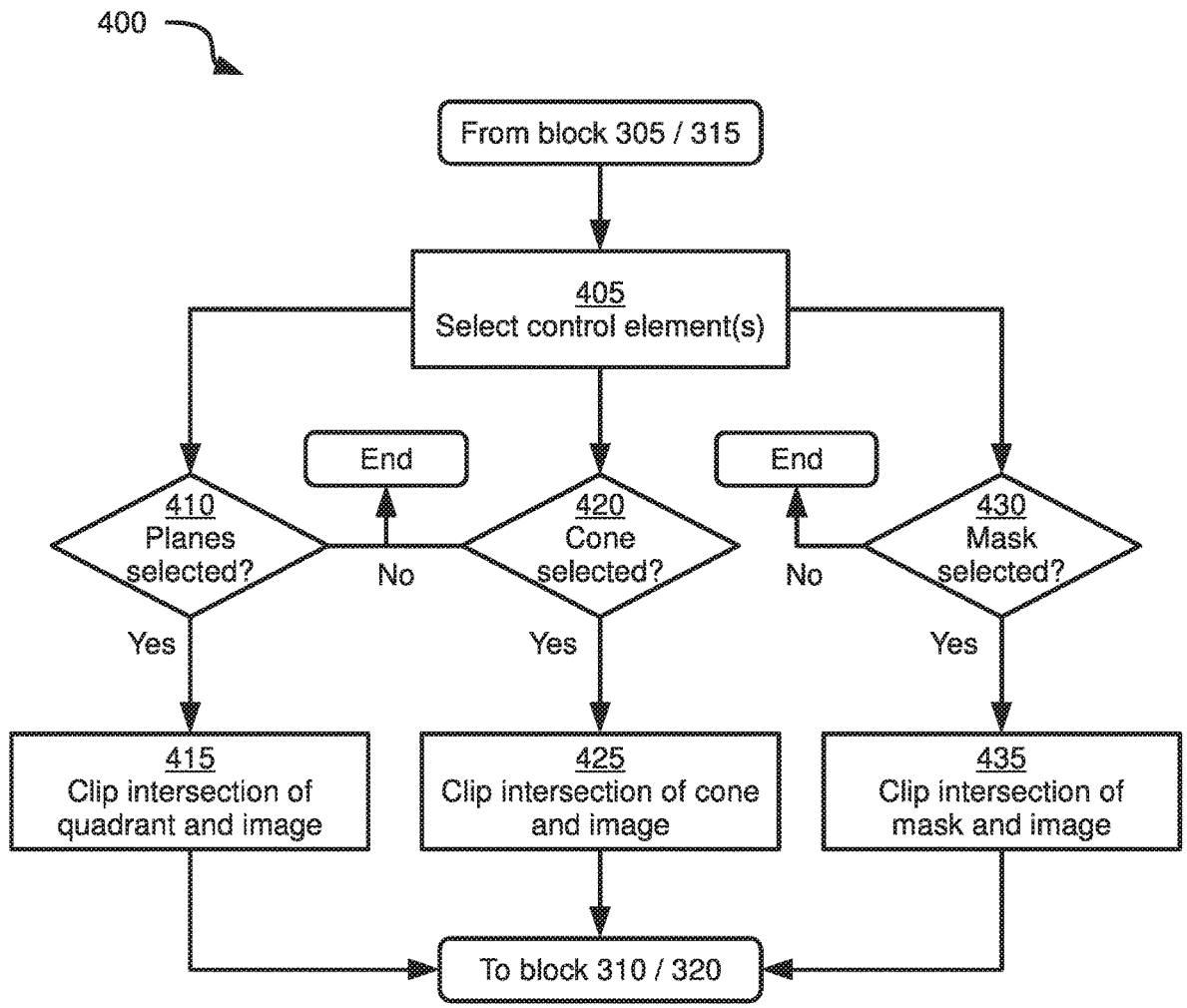
FIG. 4 depicts a method of rendering initial and further volumes in the method of FIG. 3, according to a non-limiting embodiment.

Turning now to FIGS. 4-7, three examples of control elements and the manner in which they are rendered and processed by computing device 200 will be discussed. FIG. 4 depicts a method 400, performed by computing device 200 (via the execution of application 216, discussed earlier), of performing blocks 310 and 320 (that is, the rendering steps) of method 300. Method 400 will be described with reference to FIGS. 4, 5 and 6, which depicts examples of the interfaces generated at block 310 (and, as will be seen later herein, at block 320).

Referring to FIG. 4, at block 405, having acquired the three-dimensional image, computing device 200 is configured to select one or more control elements. The definitions of the control elements are stored in memory 204, for example as part of application 216. The selection at block 405 can be automatic—for example, application 216 can contain instructions to select a default control element, or set of control elements—or the selection can be received as input data, for example from keyboard/mouse 210.

In the present example, three types of control elements are contemplated, though it will be understood that these are only examples—other types of control elements will occur to those skilled in the art in light of the present description. As seen in FIG. 4, any combination of the three types of control elements may be selected. For simplicity, the control elements will be discussed individually, however. Thus, when computing device 200 determines that the plane control elements have been selected at block 410, performance of method 400 proceeds to block 415.

The plane control elements include a plurality of planes. In the present example, three orthogonal planes are contemplated, although other numbers of planes, disposed at other angles relative to each other, may also be employed. The planes each have an initial default location relative to the three-dimensional image, such that each plane intersects the three-dimensional image. Thus, it will now be apparent that the planes, by intersecting the three-dimensional image, divide the image into quadrants (in particular, eight quadrants in the case of three orthogonal planes). At block 415, computing device 200 is configured to select one of the quadrants, and clip the intersection of that selected quadrant and the three-dimensional image, before proceeding to block 310 to render the resulting initial volume on display 110.

Figure 5:
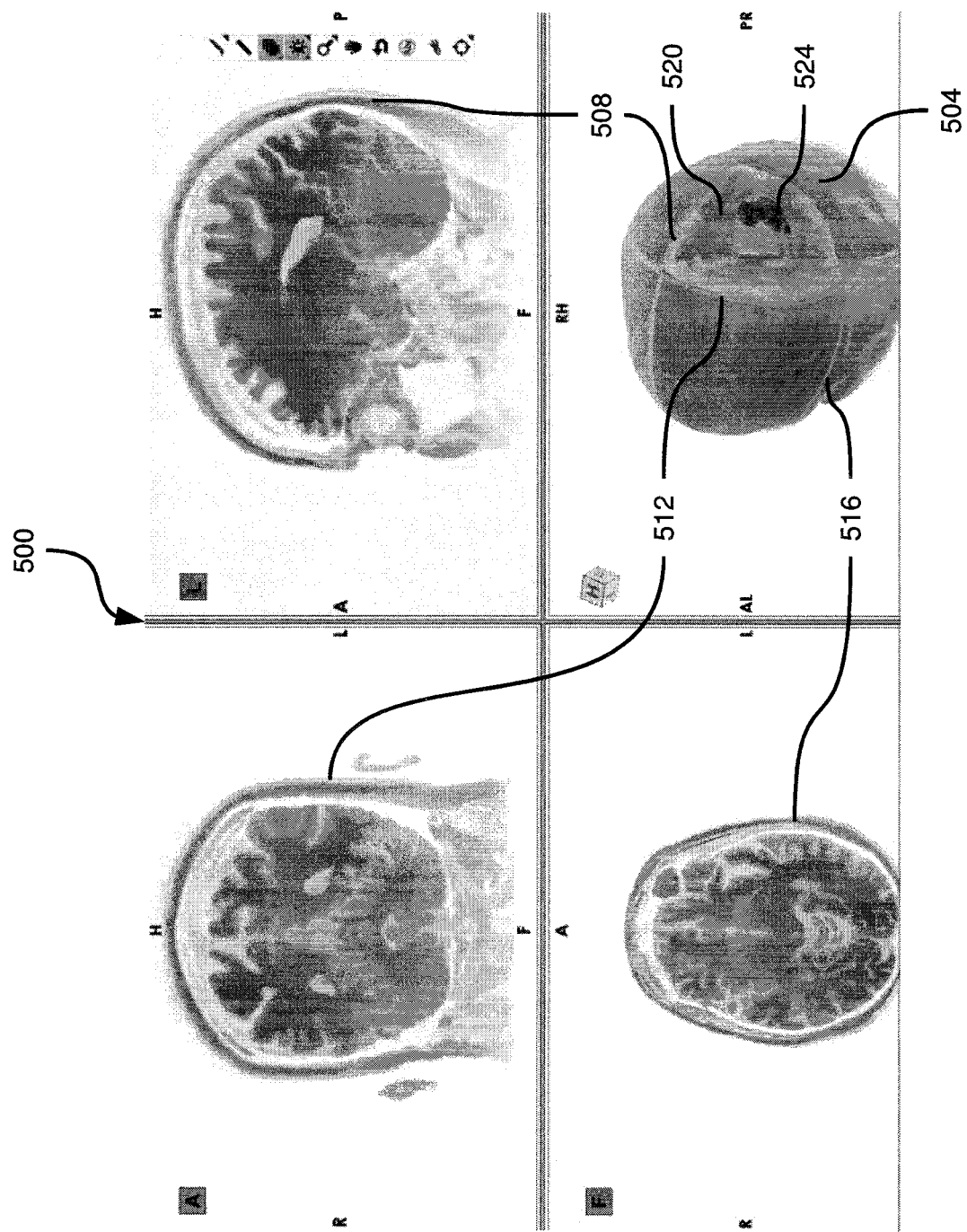
FIG. 5 depicts an example of the performance of block 310 of the method of FIG. 3, according to a non-limiting embodiment.

Referring now to FIG. 5, an example of the interface generated at block 310 following the performance of blocks 405, 410 and 415 is illustrated. FIG. 5 depicts an interface 500 generated on display 110 that includes a rendering of an initial volume 504 and control elements 508, 512 and 516 in the form of orthogonal planes. In the present example, control elements 508, 512 and 516 are the sagittal, coronal, and transverse anatomical planes, respectively. In addition to initial volume 504, two-dimensional slices of the three-dimensional image are also illustrated, each corresponding to the position of one of the three planes within the three-dimensional image. The two-dimensional views may be omitted in other embodiments.

As seen from FIG. 5, initial volume 504 includes the entire volume of the three-dimensional image (that is, the MRI scan of patient 104's head), with the exception of the portion intersected by one of the quadrants defined by planes 508, 512 and 516. The intersecting quadrant has been cut away, or clipped, and therefore is not rendered in interface 500, which allows certain interior portions of the brain to be rendered. In other words, the position of the three planes defines the outer surface of initial volume 504.

Returning to FIG. 4, whether or not the determination at block 410 is affirmative, at block 420 computing device 200 may also (or alternatively) determine that a cone control element has been selected at block 405. If the determination at block 420 is affirmative, performance of method 400 proceeds to block 425.

The cone control element is a volume in the shape of a cone, or in some embodiments, a truncated cone, having an initial default position relative to the three-dimensional image. At block 425, computing device 200 is configured to clip the portion of the three-dimensional image that intersects with the conical volume, before proceeding to block 310.

Figure 6:
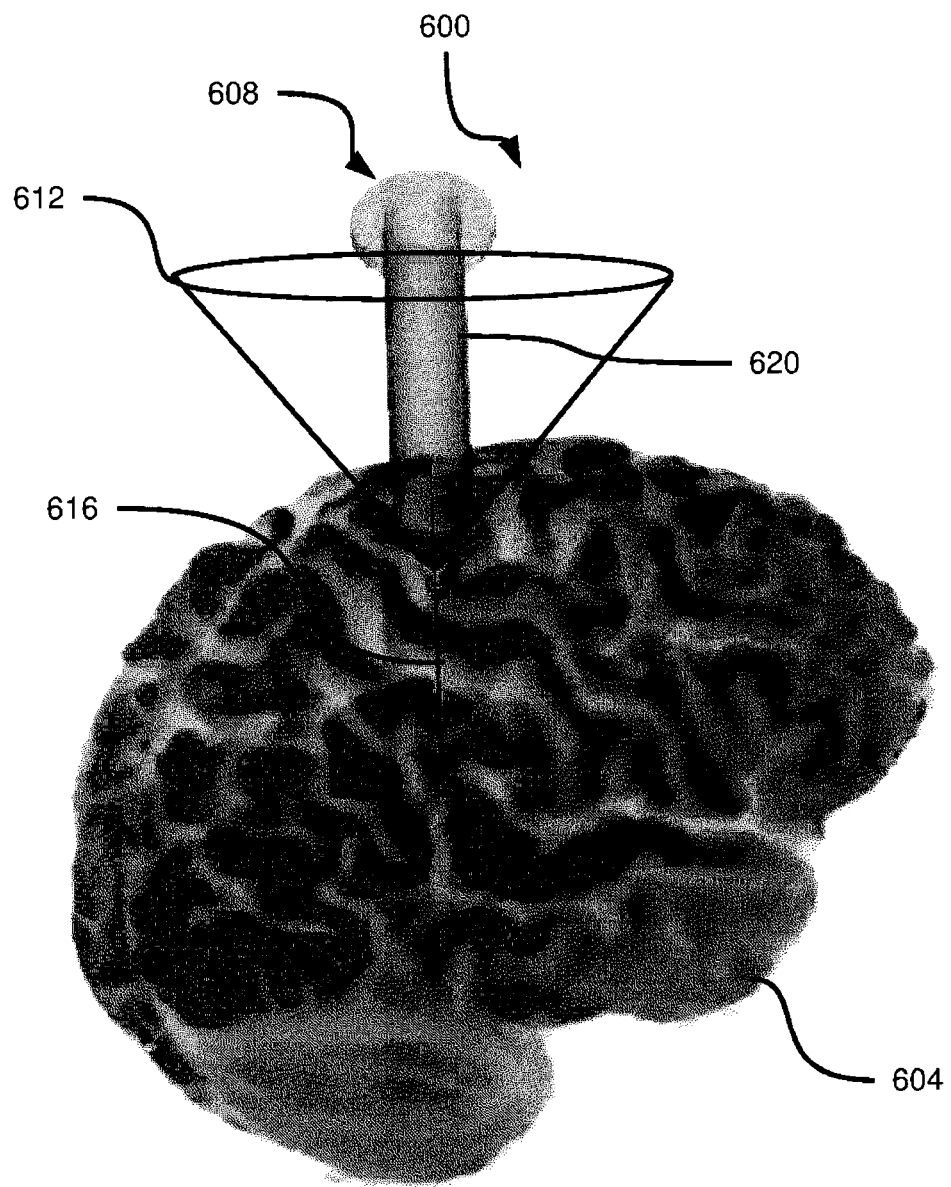
FIG. 6 depicts another example of the performance of block 310 of the method of FIG. 3, according to a non-limiting embodiment.

Turning to FIG. 6, an example interface 600 generated as a result of the performances of blocks 405, 420 and 425 is illustrated. Interface 600 includes an initial volume 604 and a control element 608. Control element 608 corresponds to a cone 612, which may be omitted from interface 600 (in the present example, cone 612 is shown in FIG. 6 only for illustrative purposes, and does not appear on interface 600). More particularly, control element 608 comprises an axis 616 along which a model 620 of an access port may be positioned at various depths relative to the three-dimensional image (and by extension, to initial volume 604). In other words, input data received at processor 204 may act to slide model 620 along axis 616. As seen in FIG. 6, the summit of cone 612 coincides with the point of model 620. Thus, as model 620 is moved along axis 616 towards the brain as represented by the three-dimensional image, cone 612 will begin to intersect with the three-dimensional image. Computing device 200 is configured to clip any portions of the three-dimensional image that intersect with cone 612. In the present example, however, the default initial position for cone 612 does not intersect with the three-dimensional image, and initial volume 604 has not had any portions clipped therefrom by computing device 200.

Returning to FIG. 4, whether or not the determinations at blocks 410 and 420 are affirmative, at block 430 computing device 200 may also (or alternatively) determine that a mask control element has been selected at block 405. If the determination at block 430 is affirmative, performance of method 400 proceeds to block 435.

The mask control element is an irregular surface having an initial default position relative to the three-dimensional image. The initial position of the mask is determined by computing device 200 by any suitable algorithm or combination of algorithms to identify the border between skull and brain. As mentioned above, images such as MRI scans generally include data depicting the entire head of patient 104, including skull and facial features. The mask control element is an estimate of the outer surface of the patient 104's brain, and divides the three-dimensional image into an "outer" part representing non-brain tissues, and an "inner" part representing brain tissues. At block 435, computing device 200 is configured to clip the portion of the three-dimensional image that intersects with the above-mentioned outer part, before proceeding to block 310. Thus, as with the plane and cone control elements, the mask control element defines the outer surface of the initial volume.

Figure 7:
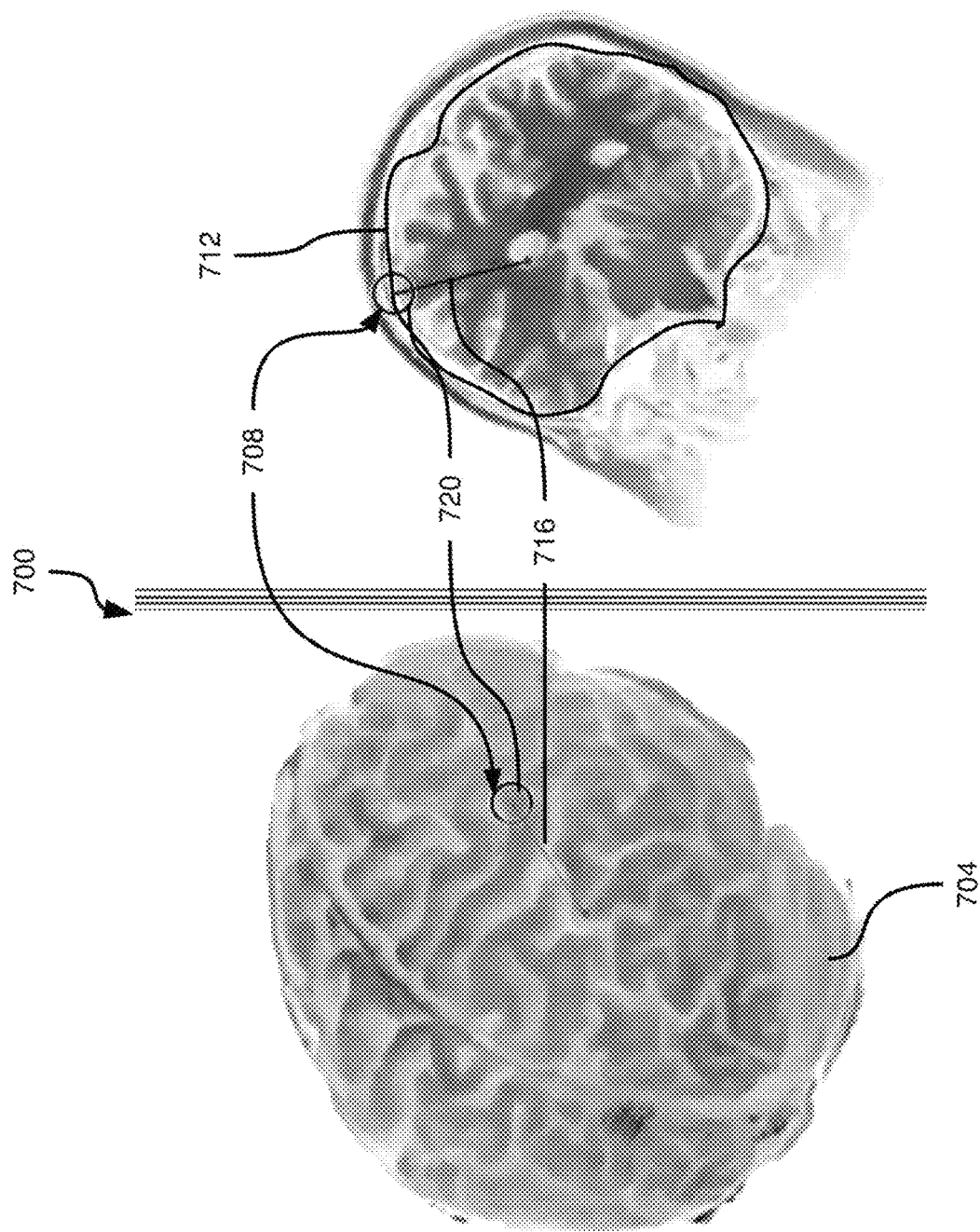
FIG. 7 depicts a further example of the performance of block 310 of the method of FIG. 3, according to a non-limiting embodiment.

Turning to FIG. 7, an example interface 700 generated as a result of the performances of blocks 405, 430 and 435 is illustrated. Interface 700 includes an initial volume 704 and a control element 708. Control element 708 corresponds to the mask, an irregular surface not illustrated in conjunction with initial volume 704. The mask, however, may be illustrated in a second two-dimensional view as an outline 712 delineating the boundary between the outer part (excluded from initial volume 704) and the inner part (included in initial volume 704). The nature of control element 708 is not particularly limited, and in the present example comprises an axis 716 and a depth indicator 720 indicating the depth of the mask along axis 716.

As mentioned earlier, the control elements described herein may be combined. For example, while interface 500 does not show the application of a mask (thus, the patient 104's skull and ears are visible in initial volume 504), interface 600 does apply the mask, in addition to cone 612.

Returning now to FIG. 3, having presented an initial interface on display 110, computing device 200 is configured to proceed to block 315. At block 315, processor 204 is configured to receive input data updating the position of the control element(s) rendered at block 310, relative to the initial volume rendered at block 310. In other words, the position of the control element(s) within the coordinate system of the three-dimensional image may change in response to input data.

Referring to FIGS. 5, 6 and 7, the input data received at block 315 can include the selection and dragging, or other repositioning, or the control elements shown therein. For example, processor 204 may receive input data from keyboard/mouse 210 representing a selection and moving operation performed on any one or more of planes 508, 512 and 516. With respect to interface 600, processor 204 may receive input data from keyboard/mouse 210 representing a change in depth of model 620 along axis 616, a change in angle of axis 616, and the like. With respect to interface 700, processor 204 may receive input data from keyboard/mouse 210 representing a change in depth of depth indicator 720 along axis 716. In further embodiments, input data can also be received form a touchscreen interface, a joystick input, a gesture control or a voice control interface.

Having received updated positions for the control elements, computing device 200 is configured, at block 320, to control display 110 to present an updated interface. The updated interface includes a rendering of a further volume of the three-dimensional image, as well as the control elements rendered in block 310, but in their updated positions. The generation of an updated interface is performed as described above in connection with method 400, substituting the updated control element positions for the previous (e.g. initial) control element positions.

Having rendered an updated interface on display 110, computing device 200 is configured to repeat blocks 315 and 320 until an exit command is received at block 325.

Figure 8A:
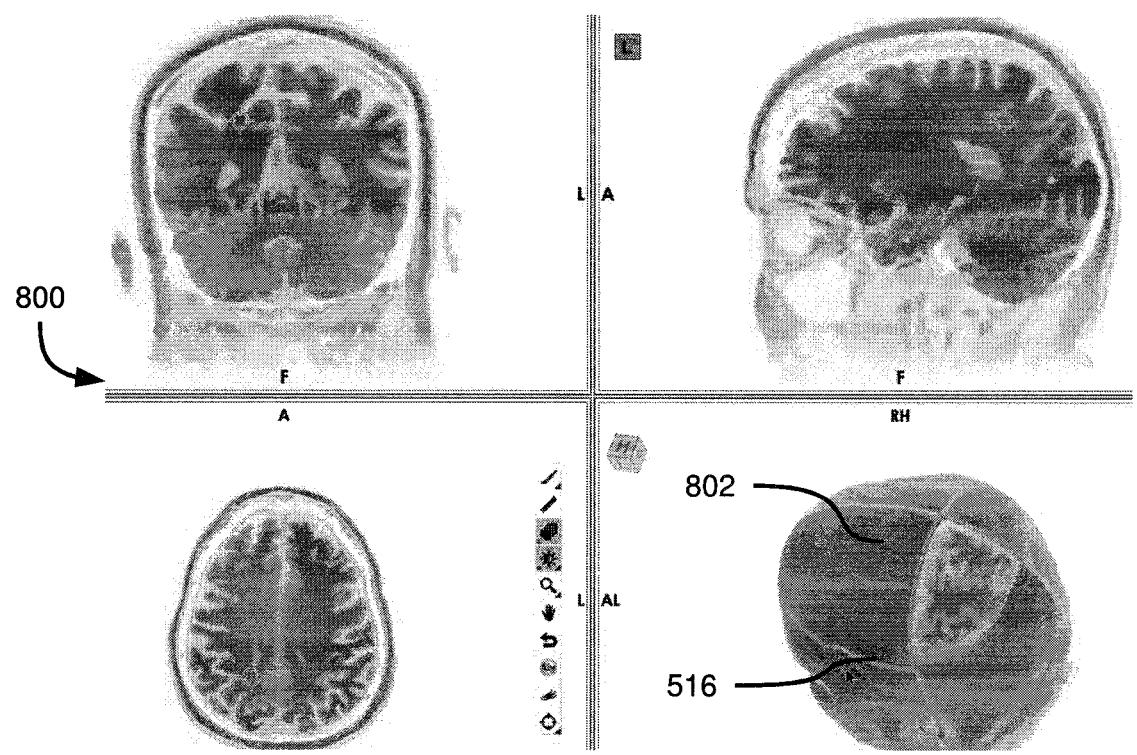
FIG. 8 depicts examples of performances of block 320, according to a non-limiting embodiment.
Figure 8B:
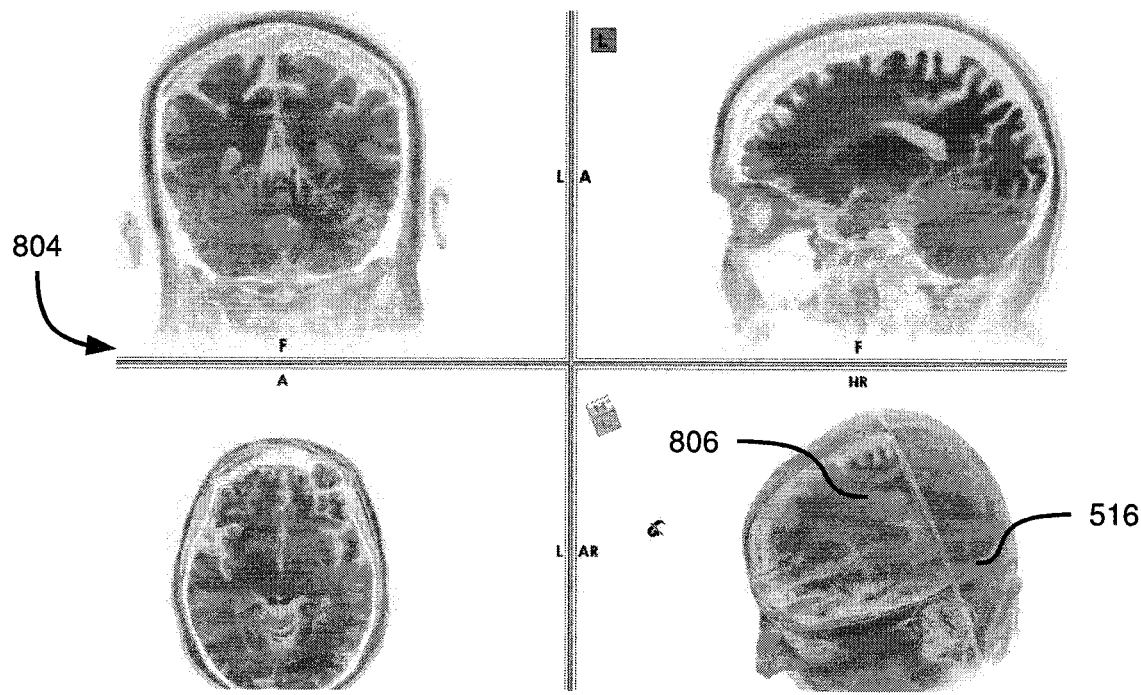

FIGS. 8A and 8B illustrate the interfaces rendered in two subsequent performances of blocks 315 and 320. FIG. 8A illustrates an interface 800 in which the position of plane 516 has been updated to raise plane 516 in the superior direction (that is, towards the top of patient 104's head as depicted by the three-dimensional image). As a result, the clipped quadrant that intersects with the three-dimensional image has changed in dimensions. In other words, the outer surface of a further volume 802 of the three-dimensional image has changed. Although the example above shows only a translation of plane 516, it is contemplated that any of the planes may also be rotated, angled and the like.

FIG. 8B illustrates another interface 804 in which plane 516 has been returned to its previous position (as shown in FIG. 5), but in which a further volume 806 has been rotated on display 110. As mentioned earlier, when the plane control elements are selected at block 405, computing device 200 is configured to select one of the quadrants defined by the intersecting planes. In the present example, computing device 200 is configured to automatically select the quadrant of which the greatest proportion is visible on display 110. Thus, for the same plane positions, different quadrants may be selected for clipping based on the position of the illustrated volume on the display.

Figure 9A:
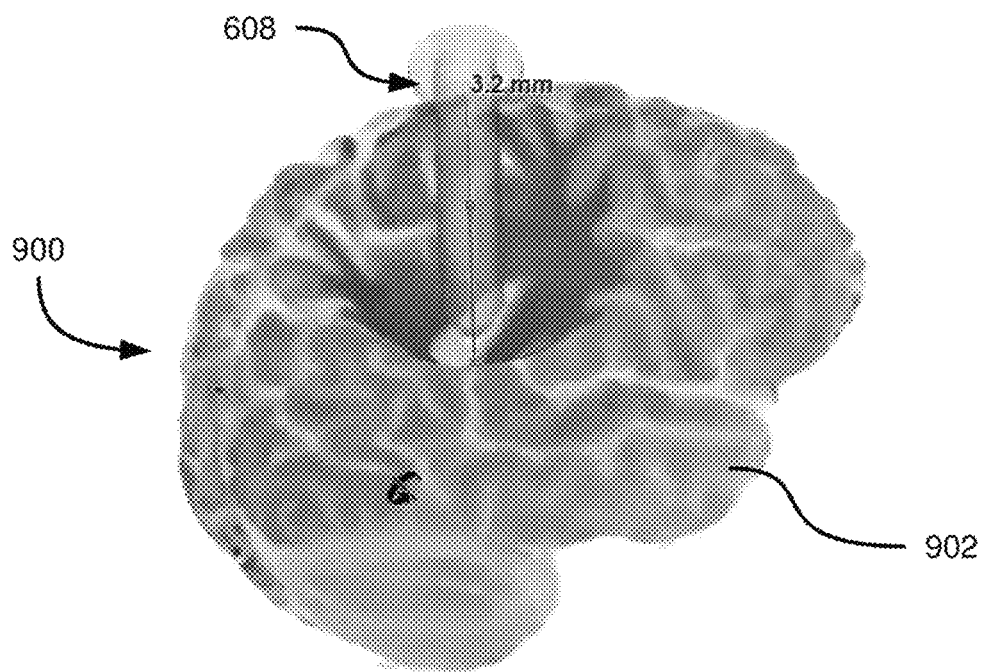
FIG. 9 depicts other examples of performances of block 320, according to a non-limiting embodiment.
Figure 9B:
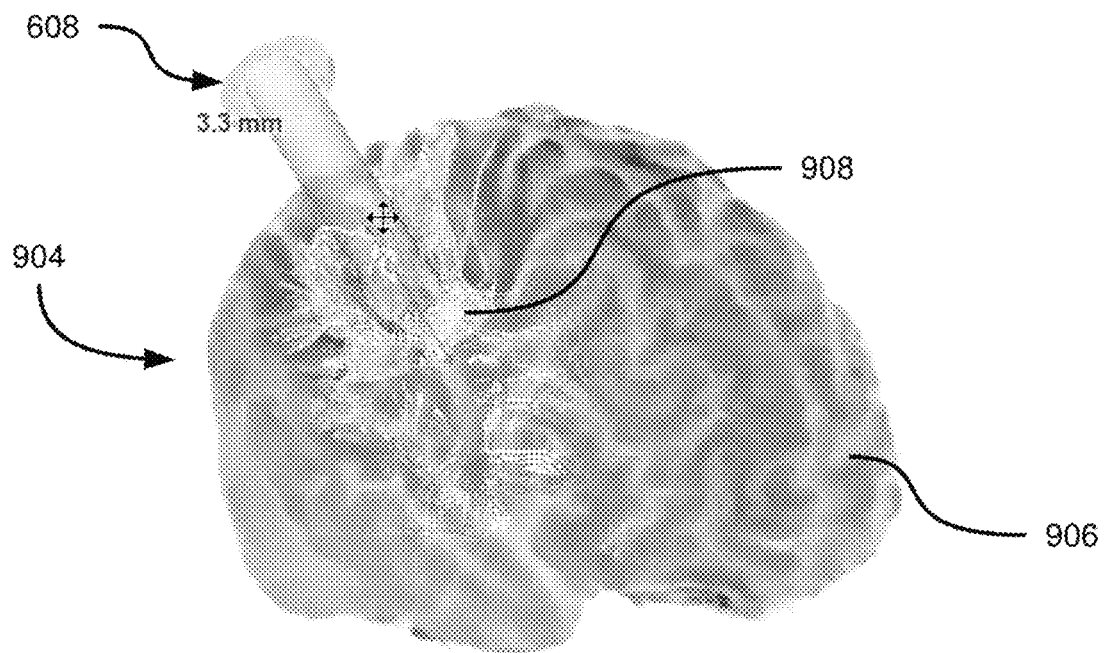

Turning to FIGS. 9A and 9B, two further interfaces generated at subsequent performances of blocks 315 and 320 are illustrated, using the cone control element. Interface 900 in FIG. 9A depicts a further volume 902 in which control element 608 has been relocated in the inferior direction (that is, model 620 has been moved down axis 616). As a result, a portion of the three-dimensional image intersects with cone 612, and the intersection portion has been clipped, resulting a cone-shaped cavity in further volume 902. Interface 904 in FIG. 9B depicts a further volume 906 which has been rotated in comparison to further volume 902. In addition, the angle of control element 608 has been altered.

Figure 10A:
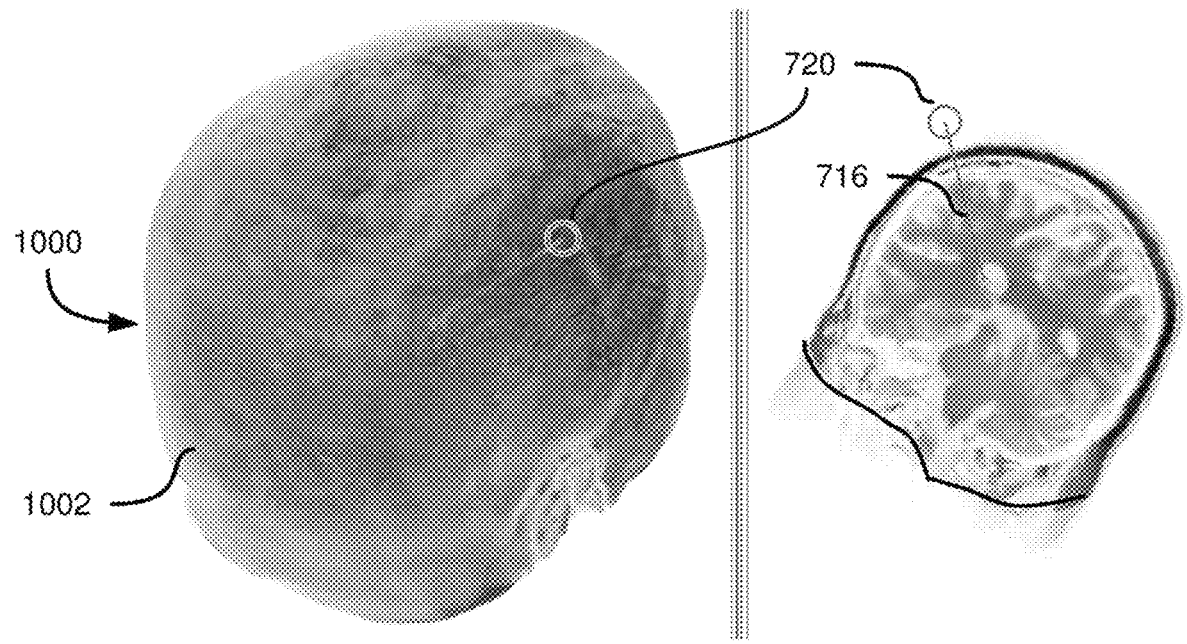
FIG. 10 depicts further examples of performances of block 320, according to a non-limiting embodiment.
Figure 10B:
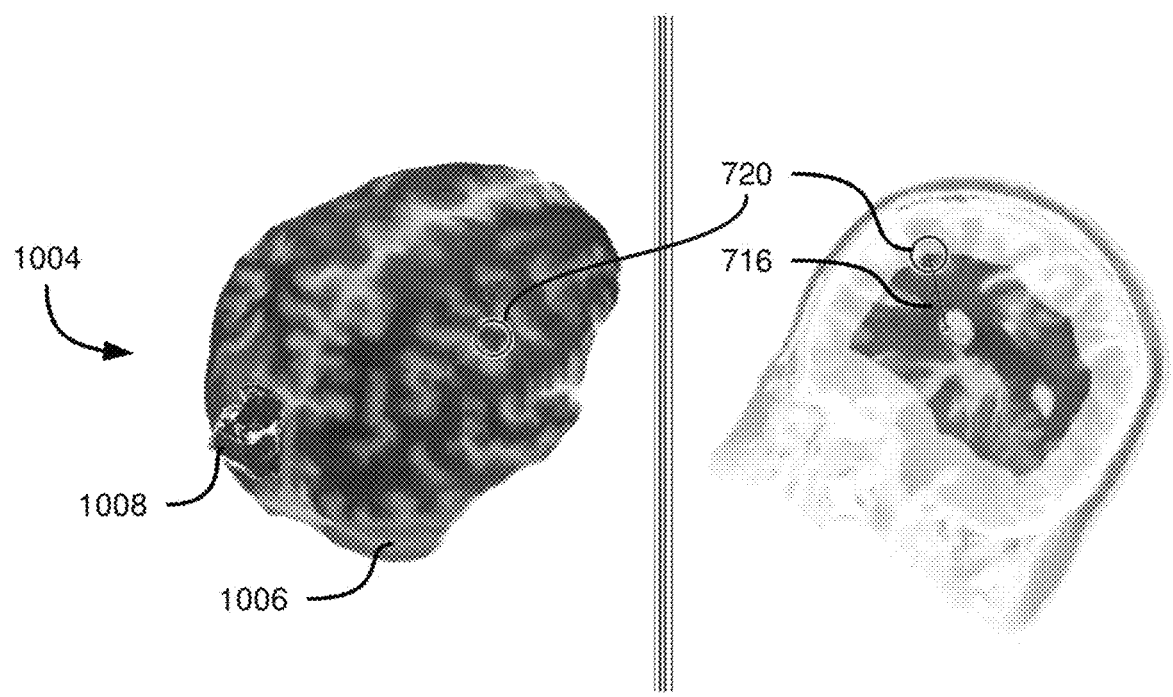

Turning to FIGS. 10A and 10B two further interfaces generated at subsequent performances of blocks 315 and 320 are illustrated, using the mask control element. Interface 1000 in FIG. 10A depicts a further volume 1002 of the three-dimensional image, in which depth marker 720 has been raised "outwards" from the brain along axis 716, in comparison with FIG. 7. Thus, the mask defined by control element 708 defines an outer surface of further volume 1002 that lies outside the outer surface of the three-dimensional image for the majority of the patient 104's skull. Thus, the skull and facial features are visible in further volume 1002, as they do not intersect with the "outer" part mentioned earlier. FIG. 10B, in contrast, depicts an interface 1004 in which depth marker 720 has been relocated inwardly along axis 716, contracting the mask and thus adjusting the outer surface of a further volume 1006. The boundary of the mask is clearly visible in FIG. 10B on the two-dimensional pane.

The adjustment of the mask depth as shown in FIGS. 10A and 10B may be implemented in a variety of ways. In the present example, the brain/skull boundary detection parameters are not altered. Rather, those parameters are set once, and computing device is configured to shift each point of the mask inwards or outwards by a number of pixels (or voxels, or any other unit of measurement within the three-dimensional image) proportional to the distance travelled by depth marker 720 along axis 716.

Variants to the techniques described above are contemplated. For example, the three-dimensional image may be supplemented by other three-dimensional images acquired by computing device 200. In some embodiments, patient data repository may contain one or more images of fluid flow tracts for patient 104, one or more images or models of a tumour within the brain of patient 104, and the like. Such images can be overlaid on the initial and further volumes discussed above. In addition, such images can be exempt from the clipping behaviour discussed above. Thus, for example, FIG. 10B shows an image 1008 of a tumour in conjunction with further volume 1006. As seen in FIG. 10B, the tumour is not subject to the masking behaviour exhibited with further volume 1006. It will now be apparent to those skilled in the art that FIG. 5 also shows an image 524 of a tumour.

As another example, FIG. 9B shows, in addition to further volume 906, an image 908 of fluid tracts. Image 908 can be a portion selected from a larger image of fluid tracts (for example, the selected portion can be limited to those tracts that would be intersected by the access port if the access port were inserted to the illustrated position of model 620).

Image overlays such as fluid tracts and tumours may be enabled and disabled by way of input data received at processor 204 (e.g. from keyboard/mouse 210). For example, the interfaces discussed above may include one or more selectable toggle elements for enabling and disabling such overlays. Other types of overlays contemplated can display or hide different types of tissue. For example, the three-dimensional image can include identifiers of which type of tissue each voxel (or group of voxels) depicts. Such identifiers may be added to the three-dimensional image manually, or by execution of a tissue identification algorithm. An interface 100 on display 110 may then include selectable elements that disable or enable the display of various portions of the three-dimensional image. In other words, an additional selection of data from the three-dimensional image can occur at or before block 310, depending on which tissue types are selected for display. In further variations, certain tissue types may be identified as being exempt from the "clipping" behaviour discussed above (similar to the illustration of the tumour model in FIG. 10B, which is exempt from the clipping imposed by the mask). Thus, the volumes mentioned above can correspond to particular tissue types, and computing device 200 can render additional volumes whose outer surfaces are not defined by control element positions (as they are exempt from clipping).

In other variations, when an interface includes a two-dimensional view, the corresponding initial or further volume (that is, the three-dimensional view) may include an illustration of the plane from which the two-dimensional view is taken. This is shown in FIG. 5; a similar mechanism can be applied to other interfaces, such as that shown in FIGS. 7, 10A and 10B.

In further variations, computing device 200 may colorize control elements to enhance their visibility on display 110. For example, the "outer" part beyond the boundary of the mask shown in FIGS. 7, 10A and 10B may be colorized differently than the inner part. As another example, each one of planes 508, 512 and 516 may be assigned a colour. The planes as illustrated on initial volume 504 and any subsequently presented further volumes, as well as in the accompanying two-dimensional views, may bear the same colours.

In other variations, some aspects of the control elements may be configurable. For example, the radius of cone 612 may be altered by processor 204 in response to input data.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

We claim:

1. A computing device comprising:
a memory;
an input device;
a display; and
a processor interconnected with the memory, the input device and the display, the processor configured to:
   acquire a three-dimensional image of a brain and a skull of a patient and store the three-dimensional image in the memory;
   obtain a boundary surface between the brain and the skull;
   render on the display (i) an initial volume of the three-dimensional image corresponding to the brain, excluding the skull, by clipping the three-dimensional image at the boundary surface, and (ii) a mask depth control element movable to adjust a clipping mask, the clipping mask having an initial position corresponding to the boundary surface;
   acquire an additional image of fluid flow tracts within the brain of the patient;
   render, on the display, an additional volume of the additional image overlaid with the initial volume, the additional volume having an outer surface that is independent of the position of the mask depth control element;
   receive, from the input device, input data updating the position of the mask depth control element of the display relative to the initial position corresponding to the boundary surface;
   responsive to receiving the input data;
      set a position of the clipping mask according to the boundary surface modified by the updated position of the mask depth control element;
      select a further volume of the three-dimensional image by clipping the three-dimensional image at a clipping mask, and
      render on the display, in place of the initial volume, the further volume of the three-dimensional image.

2. The computing device of claim 1, wherein the three-dimensional image is a magnetic resonance imaging (MRI) scan.

3. The computing device of claim 1, wherein the processor is further configured to render on the display an additional volume corresponding to a tumor; the additional volume having an outer surface that is independent of the position of the control element.

4. A method of processing images in a computing device having a memory, an input device, a display and a processor interconnected with the memory, the input device and the display, the method comprising:
   acquiring a three-dimensional image of a brain and a skull of a patient and storing the three-dimensional image in the memory;
   obtaining a boundary surface between the brain and the skull;
   at the processor, rendering on the display (i) an initial volume of the three-dimensional image corresponding to the brain, excluding the skull, by clipping the three-dimensional image at the boundary surface, and a mask depth control element movable to adjust a clipping mask, the clipping mask having an initial position corresponding to the boundary surface;
   acquiring an additional image of fluid flow tracts within the brain of the patient;
   rendering, on the display, an additional volume of the additional image overlaid with the initial volume, the additional volume having an outer surface that is independent of the position of the mask depth control element;
   receiving, at the processor from the input device, input data updating the position of the mask depth control element on the display relative to the initial position corresponding to the boundary surface;
   responsive to receiving the input data;
      setting a position of the clipping mask according to the boundary surface modified by the updated position of the mask depth control element,
      selecting a further volume of the three-dimensional image by clipping the three-dimensional image at the clipping mask; and
      controlling the display at the processor to render, in place of the initial volume, a further volume of the three-dimensional image.

5. The method of claim 4, wherein the three-dimensional image is a magnetic resonance imaging (MRI) scan.

6. The method of claim 4; further comprising rendering on the display an additional volume corresponding to a tumor, the additional volume having an outer surface that is independent of the position of the control element.

* * * * *